(12) United States Patent
Zeng et al.

(10) Patent No.: US 10,736,740 B2
(45) Date of Patent: Aug. 11, 2020

(54) TRANSCATHETER PULMONARY BALL VALVE ASSEMBLY

(71) Applicant: VENUS MEDTECH (HANGZHOU), INC., Hangzhou, Zhejiang (CN)

(72) Inventors: Min Frank Zeng, Irvine, CA (US); Pham Lo, Irvine, CA (US)

(73) Assignee: Venus Medtech (Hangzhou) Inc., Hangzhou (CN)

( * ) Notice: Subject to any disclaimer, the term of this patent is extended or adjusted under 35 U.S.C. 154(b) by 0 days.

(21) Appl. No.: 16/104,812

(22) Filed: Aug. 17, 2018

(65) Prior Publication Data

US 2019/0000616 A1 Jan. 3, 2019

Related U.S. Application Data

(63) Continuation of application No. 15/377,765, filed on Dec. 13, 2016, now Pat. No. 10,052,202, which is a continuation-in-part of application No. 14/720,885, filed on May 25, 2015, now abandoned.

(51) Int. Cl.
*A61F 2/24* (2006.01)

(52) U.S. Cl.
CPC .... *A61F 2/2418* (2013.01); *A61F 2220/0075* (2013.01); *A61F 2230/0069* (2013.01); *A61F 2230/0093* (2013.01)

(58) Field of Classification Search
CPC .................. A61F 2/2418; A61F 2/2412; A61F 2230/0093; A61F 2230/0069
See application file for complete search history.

(56) References Cited

U.S. PATENT DOCUMENTS

| | | | | |
|---|---|---|---|---|
| 2011/0313515 | A1* | 12/2011 | Quadri | A61F 2/2418 623/2.2 |
| 2014/0277427 | A1* | 9/2014 | Ratz | A61F 2/2409 623/2.38 |
| 2015/0196390 | A1* | 7/2015 | Ma | A61F 2/2418 623/2.17 |

* cited by examiner

*Primary Examiner* — Brian A Dukert
(74) *Attorney, Agent, or Firm* — Raymond Sun

(57) ABSTRACT

A heart valve assembly has a frame comprising an anchoring section, a generally cylindrical leaflet support section, and a neck section that transitions between the anchoring section and the valve support section. The anchoring section has a ball-shaped configuration defined by a plurality of wires that extend from the leaflet support section, with each wire extending radially outwardly to a vertex area where the diameter of the anchoring section is at its greatest, and then extending radially inwardly to a hub. A plurality of leaflets are stitched to the leaflet support section. The heart valve assembly is delivered to the location of a native pulmonary trunk, the vertex area of the anchoring section is deployed into the native pulmonary arteries such that the vertex area is retained in the pulmonary arteries, and then the leaflet support section is deployed in the pulmonary trunk.

20 Claims, 13 Drawing Sheets

TRANSCATHETER PULMONARY BALL VALVE ASSEMBLY

RELATED CASES

This is a continuation-in-part of co-pending application Ser. No. 14/720,885, filed May 25, 2015, whose entire disclosure is incorporated by this reference as though set forth fully herein.

BACKGROUND OF THE INVENTION

Field of the Invention

The present invention is directed to methods, systems and apparatus for transcatheter placement of a pulmonary valve to restore pulmonary valve function in a patient.

Description of the Prior Art

Patients with congenital heart defects involving the right ventricular outflow tract (RVOT), such as Tetralogy of Fallot, Truncus Arteriosus, and Transposition of the Great Arteries, are commonly treated by surgical placement of an RVOT conduit between the right ventricle (RV) and pulmonary artery (PA). However, despite advances in terms of durability, the lifespan of RVOT conduits is relatively limited, and most patients with congenital RVOT defects are committed to multiple cardiac surgeries over their lifetime.

Common failure modes for conduits include calcification, intimal proliferation, and graft degeneration, which result in stenosis and regurgitation, alone or in combination. Both stenosis and regurgitation place an increased hemodynamic burden on the right ventricle, and can result in reduced cardiac function. Percutaneous placement of stents within the conduit can provide palliative relief of stenosis, and may eliminate or postpone the need for surgery. However, stent placement is only useful to treat conduit stenosis. Patients with predominant regurgitation or mixed stenosis and regurgitation cannot be adequately treated with stents.

Although pulmonary regurgitation is generally well tolerated for many years when the pulmonary vasculature is normal, long-term follow-up has revealed its detrimental effect on right and left ventricular function. Chronic volume overload of the RV leads to ventricular dilatation and impairment of systolic and diastolic function, which in the long term leads to reduced exercise tolerance, arrhythmias, and an increased risk of sudden death. Restoration of pulmonary valve competence at an appropriate time has resulted in improvement of right ventricular function, incidence of arrhythmias, and effort tolerance. However, if RV dilation progresses beyond a certain point, reportedly to an RV end-diastolic volume on the order of 150-170 mL/m$^2$, normalization of RV size may not be possible, even with pulmonary valve placement. This finding suggests that the benefits of restoring pulmonary valve competence may be greatest when the RV retains the capacity to remodel, and that earlier pulmonary valve replacement may be optimal.

Until recently, the only means of restoring pulmonary valve competence in patients with a regurgitant conduit has been surgical valve or conduit replacement. Although this treatment is generally effective in the short-term, with low mortality, open heart surgery inevitably entails risks, including the acute risks of cardiopulmonary bypass, infection, bleeding, and postoperative pain, as well as the chronic impact on the myocardium and brain. Furthermore, adolescents and adults are reluctant to undergo reoperation where the longevity of the new conduit does not guarantee freedom from future operations. Thus, a less invasive treatment for conduit dysfunction would be welcomed by patients and their families, and may allow safe, earlier intervention for conduit dysfunction that mitigate the negative effects of chronic volume and pressure loading of the RV.

Thus, there remains a need for effective treatment congenital heart defects involving the right ventricular outflow tract (RVOT).

SUMMARY OF THE DISCLOSURE

The present invention provides a pulmonary valve assembly and associated delivery system that allows percutaneous transcatheter placement of a biological valve within a self-expanding stent at the RVOT for a patient. The pulmonary valve assembly restores pulmonary valve function in patients with a dysfunctional RVOT conduit and a clinical indication for pulmonary valve replacement. Unlike currently available options for pulmonary valve replacement, the pulmonary valve assembly of the present invention is intended to be placed inside a percutaneous transcatheter delivery system, and thus does not require implantation or deployment through invasive surgical procedures.

The present invention provides a heart valve assembly comprising a frame comprising an anchoring section, a generally cylindrical leaflet support section, and a neck section that transitions between the anchoring section and the valve support section. The anchoring section has a circumferential vertex area defined by a plurality of wires that extend from the leaflet support section, with each wire extending radially outwardly to the vertex area, and then extending radially inwardly to a hub. The anchoring section further includes a plurality of umbrella segments that extend radially outwardly from the hub and having a circumferential diameter that is greater than the circumferential diameter of the vertex area. A plurality of leaflets are stitched to the leaflet support section.

The present invention provides a method for securing the heart valve assembly in the pulmonary trunk of a human heart. The heart valve assembly is delivered to the location of a native pulmonary trunk, the vertex area of the anchoring section is deployed into the native pulmonary arteries such that the vertex area is retained in the pulmonary arteries, and then the leaflet support section is deployed in the pulmonary trunk.

DETAILED DESCRIPTION OF THE PREFERRED EMBODIMENTS

Figure 1:
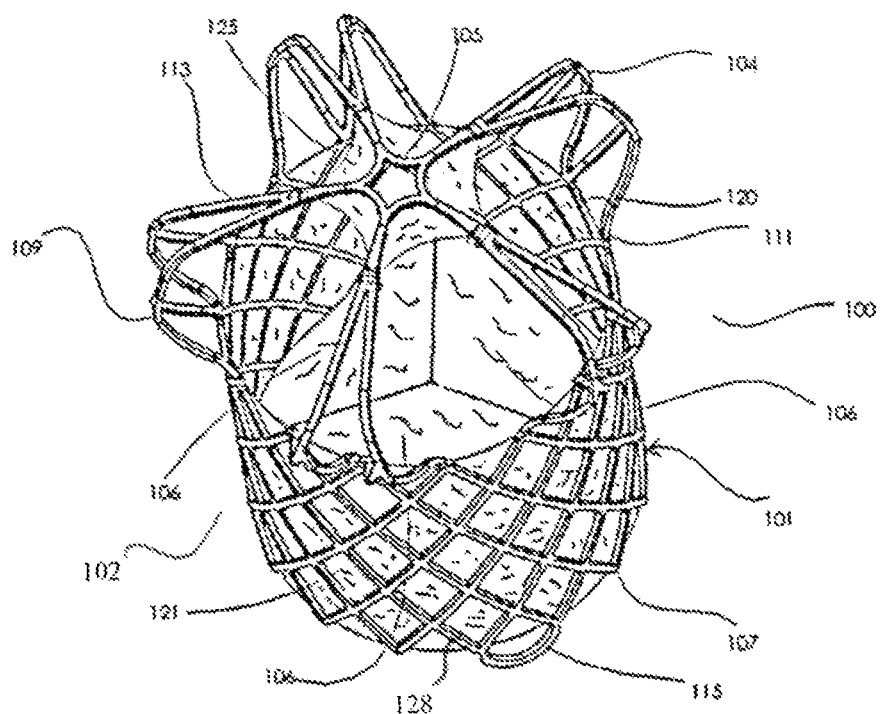
FIG. 1 is a perspective side view of a pulmonary valve assembly according to one embodiment of the present invention shown in an expanded configuration.
Figure 2:
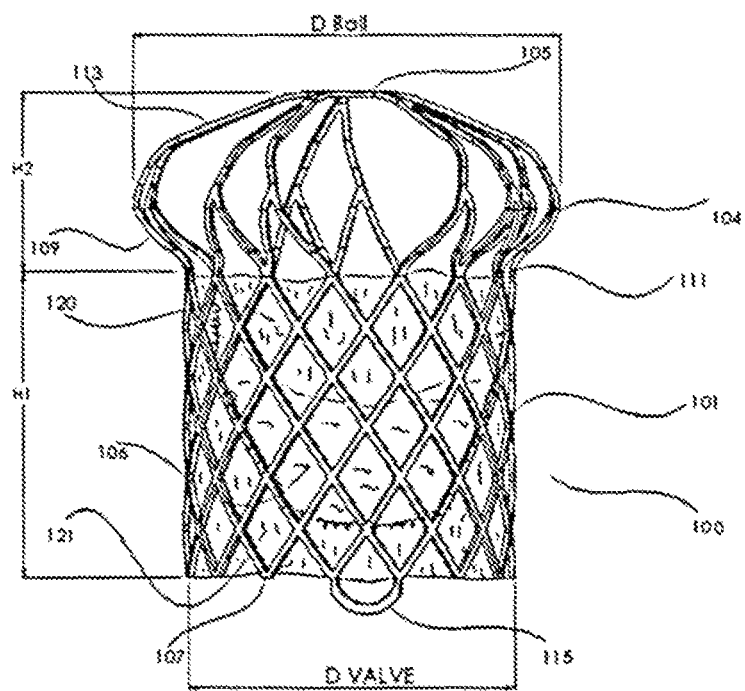
FIG. 2 is a side view of the assembly of FIG. 1.
Figure 3:
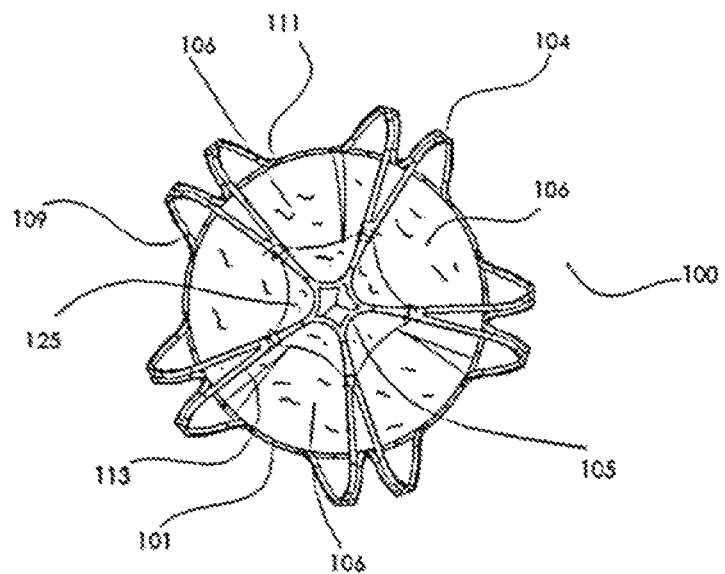
FIG. 3 is a top view of the assembly of FIG. 1.
Figure 4:
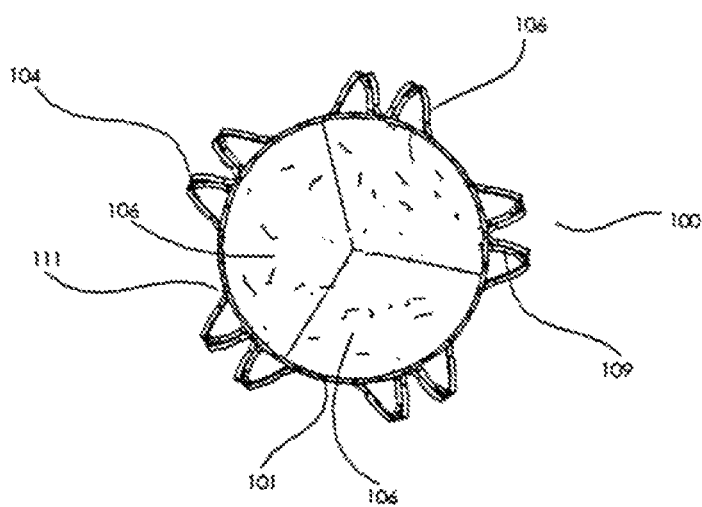
FIG. 4 is a bottom view of the assembly of FIG. 1.
Figure 5:
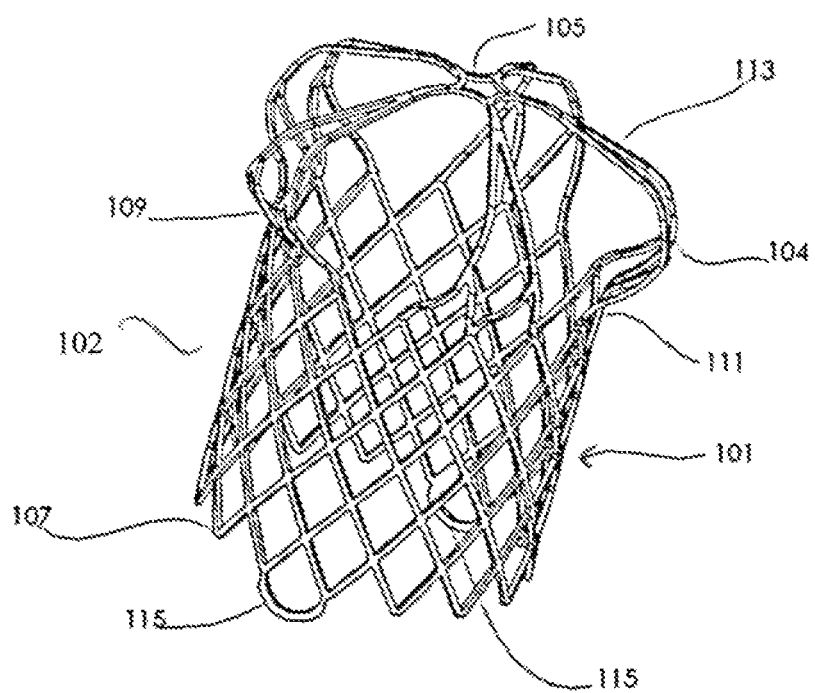
FIG. 5 is a perspective side view of the frame of the assembly of FIG. 1.
Figure 6:
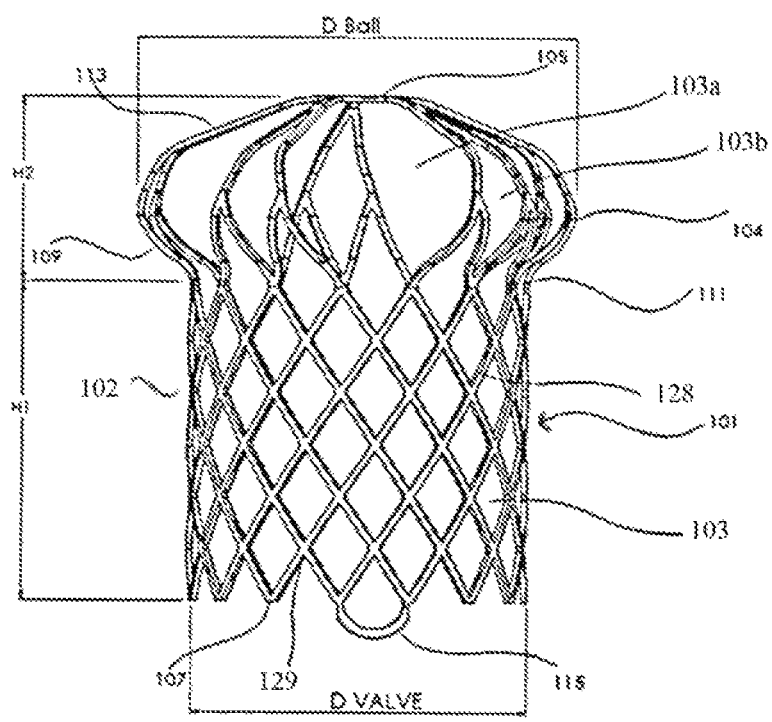
FIG. 6 is a side view of the frame of FIG. 5.

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

The present invention provides a pulmonary valve assembly 100 that is shown in fully assembled form in FIGS. 1-4. The assembly 100 has a frame 101 (see FIGS. 5-8) that has an anchoring section 109 and a leaflet support section 102 that is adapted to carry an integrated leaflet assembly that comprises a plurality of leaflets 106. The assembly 100 can be effectively secured at the native pulmonary trunk area. The overall construction of the assembly 100 is simple, and effective in promoting proper mitral valve function.

As shown in FIGS. 5-8, the frame 101 has a ball-shaped anchoring section 109 that transitions to a leaflet support section 102 via a neck section 111. The different sections 102, 109 and 111 can be made of one continuous wire, and can be made from a thin wall biocompatible metallic element (such as stainless steel, Co—Cr based alloy, Nitinol™, Ta, and Ti etc.). As an example, the wire can be made from a Nitinol™ wire that is well-known in the art, and have a diameter of 0.2" to 0.4". These sections 109, 102 and 111 define open cells 103 within the frame 101. Each cell 103 can be defined by a plurality of struts 128 that encircle the cell 102. In addition, the shapes and sizes of the cells 103 can vary between the different sections 109, 102 and 111. For example, the cells 103 for the leaflet support section 102 are shown as being diamond-shaped.

Figure 7:
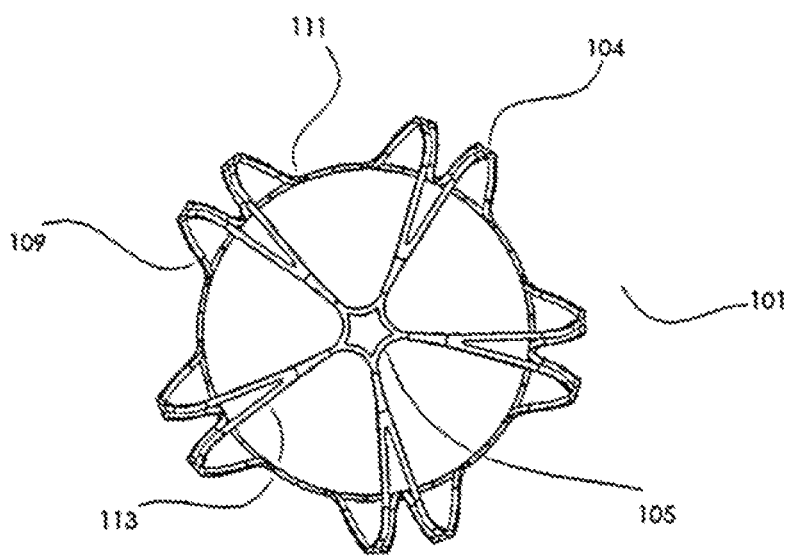
FIG. 7 is a top view of the frame of FIG. 5.
Figure 8:
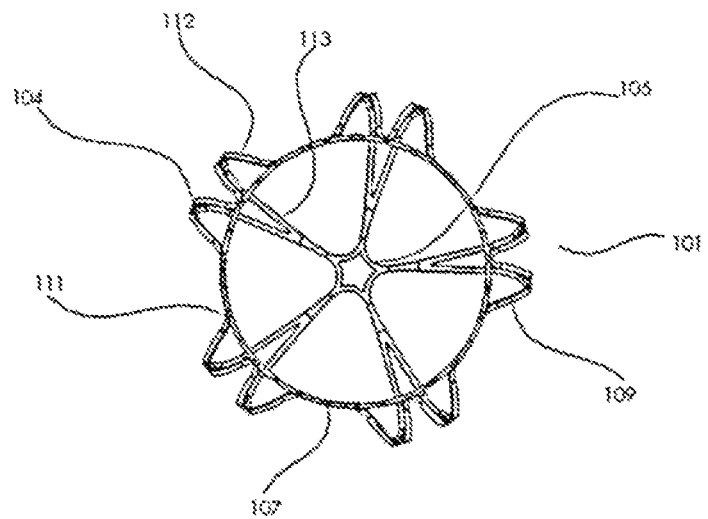
FIG. 8 is a bottom view of the frame of FIG. 5.
Figure 9A:
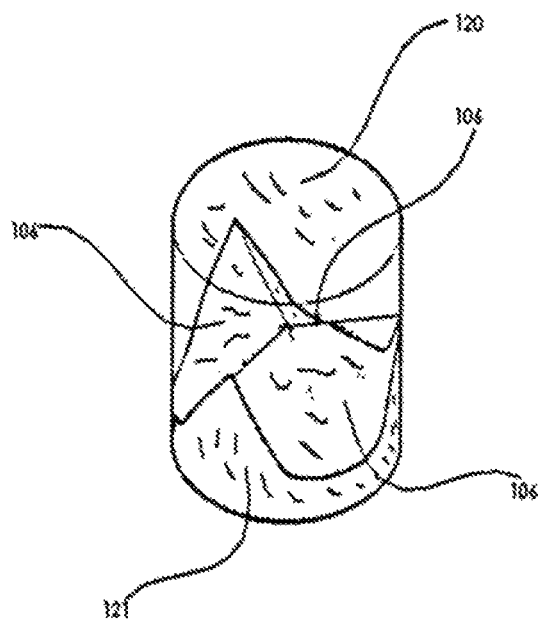
FIG. 9A is a perspective view of the leaflet assembly of the pulmonary valve assembly of FIG. 1.
Figure 9B:
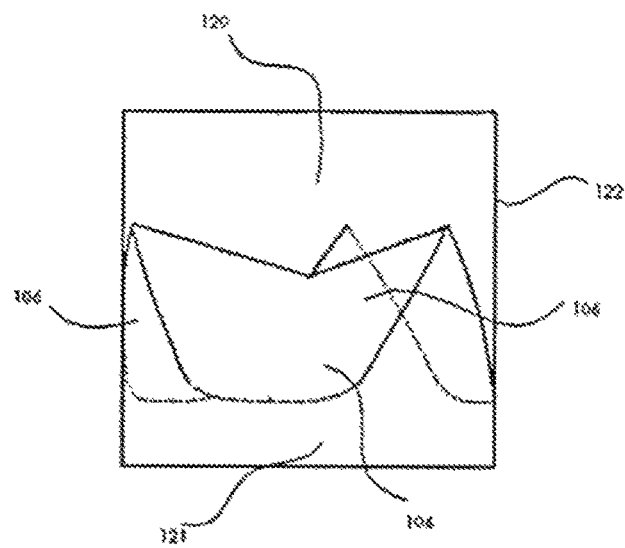
FIG. 9B is a side view of the leaflet assembly of FIG. 9A.

The leaflet support section 102 is generally cylindrical, functions to hold and support the leaflets 106, and has an inflow end that is configured with an annular zig-zag arrangement of inflow tips 107. The zig-zag arrangement defines peaks (i.e., the tips 107) and valleys (inflection points 129). In addition, ears 115 are provided opposite to each other at the inflow end, with each ear 115 formed by a curved wire portion connecting two adjacent tips 107. As shown in FIG. 1, the leaflets 106 can be sewn directly to the struts 128 of the cells 103 in the leaflet support section 102. The outflow end of the leaflet support section 102 transitions to the anchoring section 109 via a neck section 111 that also functions as an outflow end for the leaflet support section 102. The anchoring section 109 functions to secure or anchor the assembly 100, and specifically the frame 101, to the pulmonary trunk of the human heart. The anchoring section 109 has a ball-shaped configuration defined by a plurality of wires 113 that extend from a cell 103 in the leaflet support section 102, with each wire 113 extending radially outwardly to a vertex area 104 where the circumferential diameter of the anchoring section 109 is at its greatest, and then extending radially inwardly to a hub 105. As best shown in FIG. 7, adjacent pairs of wires 113 converge towards a connection point at their upper ends before the connection point merges into the hub 105. This arrangement results in the anchoring section 109 have alternating large cells 103a and smaller cells 103b. See FIG. 6.

All portions of the anchoring section 109 have a wider diameter than any portion of the leaflet support section 102 or the neck section 111.

The following are some exemplary and non-limiting dimensions for the frame 101. For example, referring to FIGS. 2 and 6, the height H1 of the leaflet support section 102 can be between 25-30 mm; the height H2 of the anchoring section 109 can be between 7-12 mm; the diameter Dball of the anchoring section 109 at the vertex area 104 can be between 40-50 mm; and the diameter DVALVE of the leaflet support section 102 can be between 24-34 mm.

In addition, the length of the leaflet support section 102 can vary depending on the number of leaflets 106 supported therein. For example, in the embodiment illustrated in FIGS. 1-4 where three leaflets 106 are provided, the length of the leaflet support section 102 can be about 10-15 mm. If four leaflets 106 are provided, the length of the leaflet support section 102 can be shorter, such as 8-10 mm. These exemplary dimensions can be used for an assembly 100 that is adapted for use at the native pulmonary tract for a generic adult.

Referring now to FIGS. 1-4 and 9A-9B, the leaflet assembly is made up of a tubular skirt 122, a top skirt 120, and a bottom skirt 121, with a plurality of leaflets sewn or otherwise attached to the tubular skirt 122 inside the channel defined by the tubular skirt 122. The tubular skirt 122 can be stitched or sewn to the struts 128. A separate ball skirt 125 can be sewn or stitched to the hub 105. The leaflets 106 and the skirts 120, 121, 122 and 125 can be made of the same material. For example, the material can be a treated animal tissue such as pericardium, or from biocompatible polymer material (such as PTFE, Dacron, bovine, porcine, etc.), The leaflets 106 and the skirts 120, 121, 122 and 125 can also be provided with a drug or bioagent coating to improve performance, prevent thrombus formation, and promote endothelialization, and can also be treated (or be provided) with a surface layer/coating to prevent calcification.

The assembly 100 of the present invention can be compacted into a low profile and loaded onto a delivery system, and then delivered to the target location by a non-invasive medical procedure, such as through the use of a delivery catheter through transapical, or transfemoral, or transseptal procedures. The assembly 100 can be released from the delivery system once it reaches the target implant site, and can expand to its normal (expanded) profile either by inflation of a balloon (for a balloon expandable frame 101) or by elastic energy stored in the frame 101 (for a device where the frame 101 is made of a self-expandable material).

Figure 10:
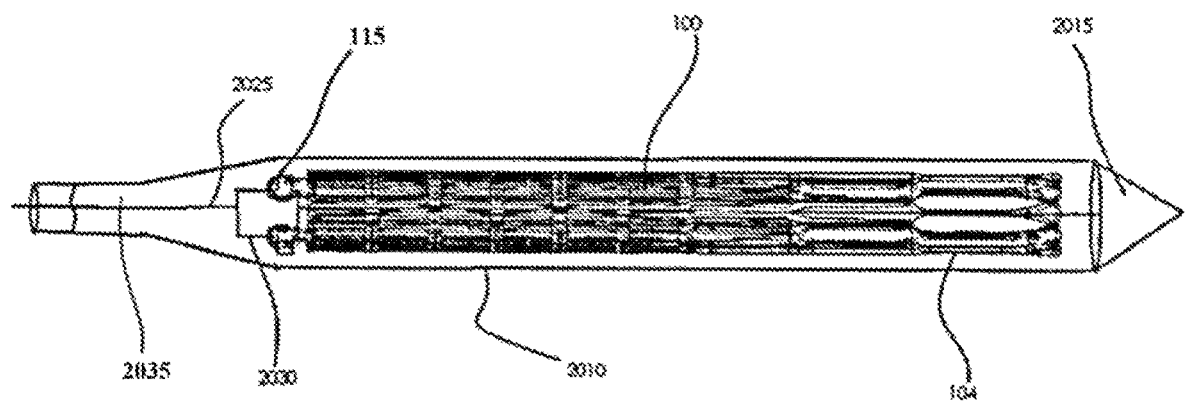
FIG. 10 illustrates a delivery system that can be used to deploy the assembly of FIG. 1.
Figure 11:
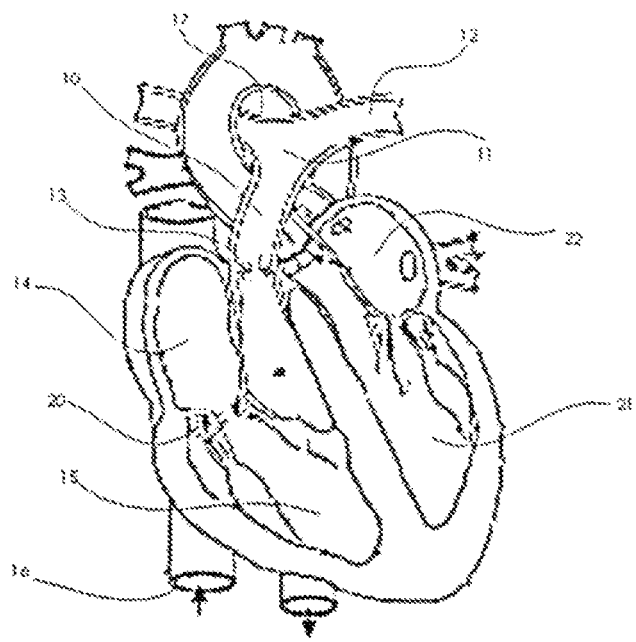
FIG. 11 illustrates a cross-section of a human heart.

FIGS. 12-16 illustrate how the assembly 100 can be deployed at the pulmonary trunk of a patient's heart using a transapical delivery. FIG. 11 illustrates the various anatomical parts of a human heart, including the pulmonary trunk 10, the left pulmonary artery 12, the junction 11 of the pulmonary arteries, the pulmonary valve 13, the topwall pulmonary artery 17, the right atrium 14, the right ventricle 15, the tricuspid valve 20, the left ventricle 21, and the left atrium 22. Referring now to FIG. 10, the delivery system includes a delivery catheter having an outer shaft 2035, and an inner core 2025 extending through the lumen of the outer shaft 2035. A pair of ear hubs 2030 extends from the inner core 2025, and each ear hub 2030 is also connected to a distal tip 2105. Each ear hub 2030 is connected (e.g., by stitching) to one ear 115 of the frame 101. A capsule 2010 is connected to and extends from the distal end of the outer shaft 2035 and is adapted to surround and encapsulate the assembly 100. A shaft extends from the struts 128 through the internal lumen of the assembly 100 to a distal tip 2015. The device 100 is crimped and loaded on the inner core 2025, and then covered by the capsule 2010.

Figure 12:
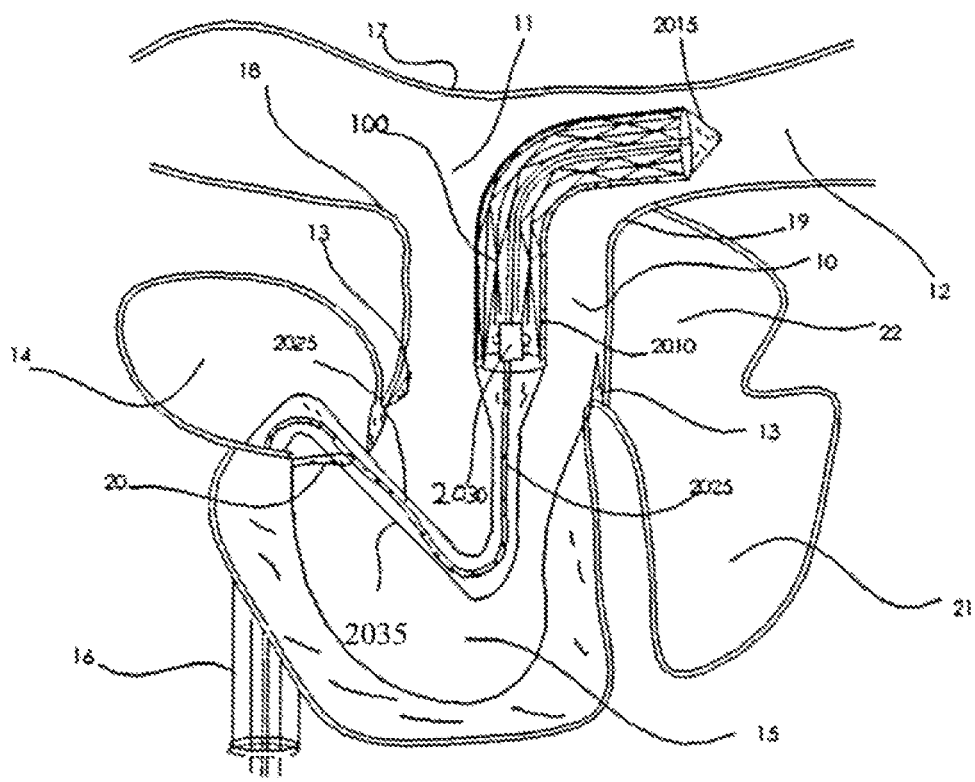
FIGS. 12-16 illustrate how the assembly of FIG. 1 can be deployed in the pulmonary trunk of a patient's heart using a transapical delivery system.
Figure 13:
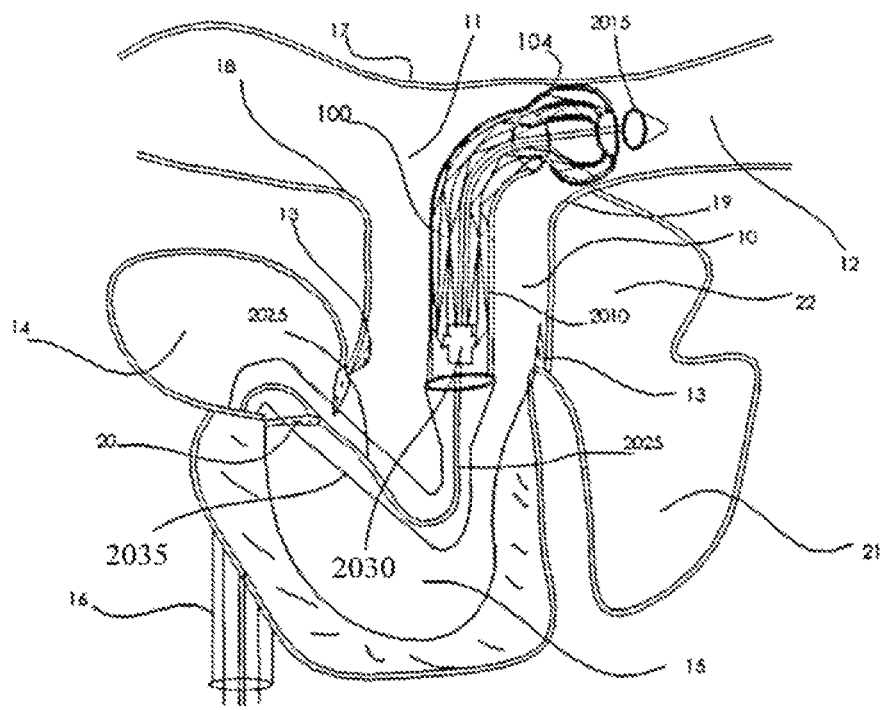
Figure 14:
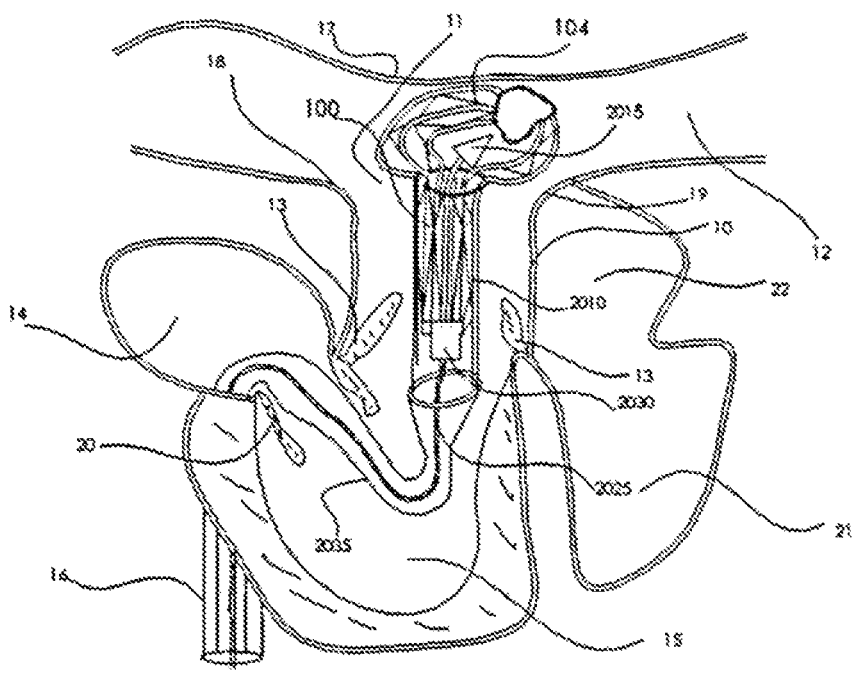
Figure 15:
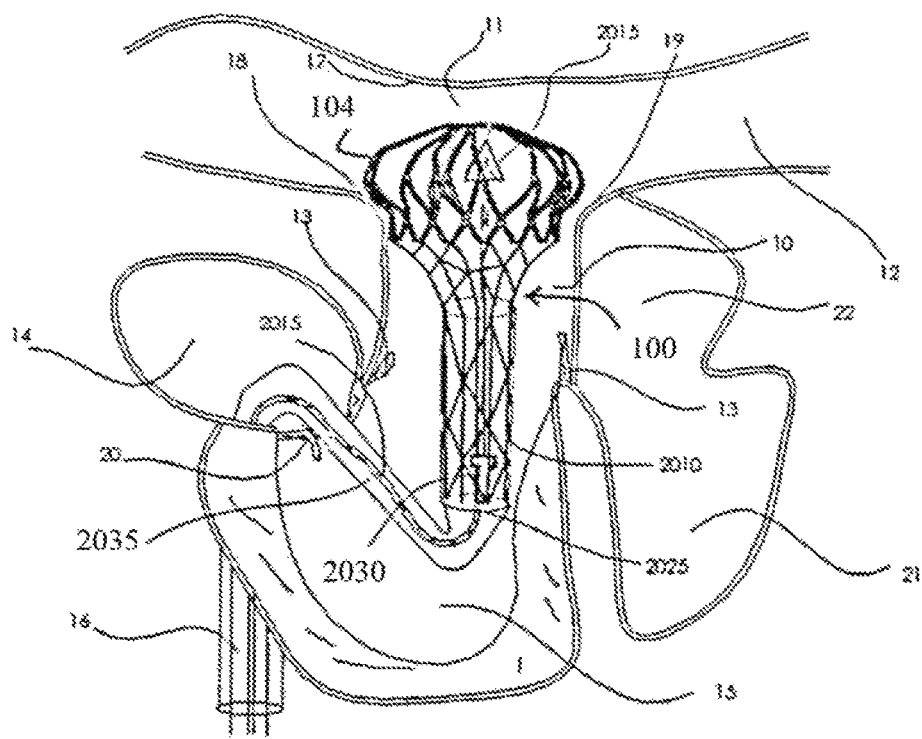
Figure 16:
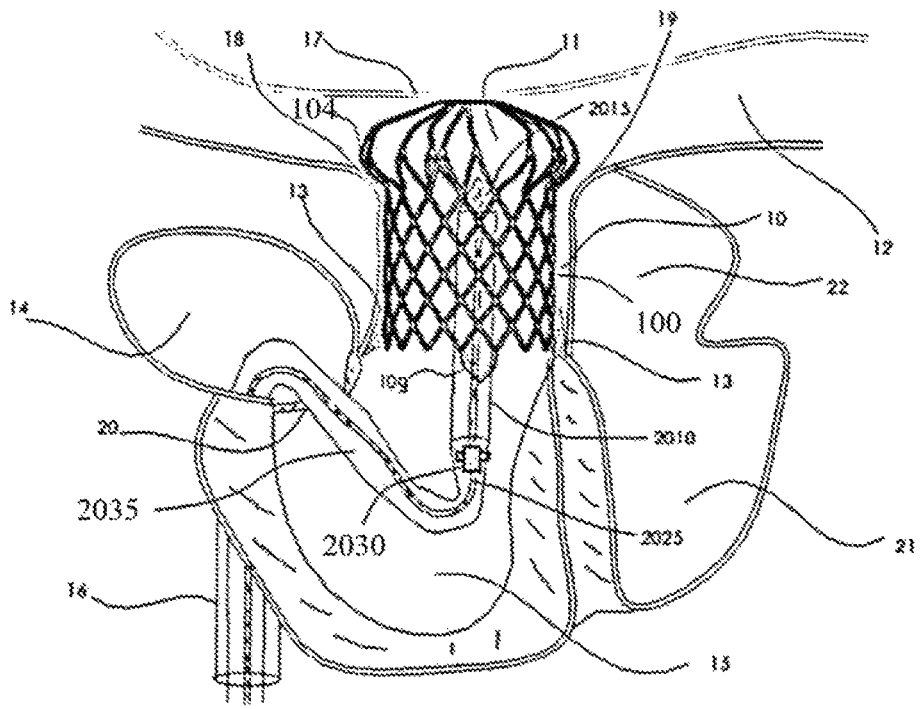

Referring now to FIG. 12, the assembly 100 is shown in a collapsed configuration being navigated up the pulmonary trunk 10 via the right femoral vein and into a part of the left pulmonary artery 12. In FIG. 13, the capsule 2010 is partially withdrawn with respect to the inner core 2025 (and the assembly 100 that is carried on the inner core 2025) to partially expose the assembly 100 so that the self-expanding frame 101 will deploy a portion of the anchoring section 109 in the left pulmonary artery 12 at a location adjacent the pulmonary trunk 10. As the capsule 2010 is further withdrawn, the remainder of the anchoring section 109 is completely deployed into the upper region of the pulmonary trunk 10 which branches into the pulmonary arteries, with the vertex area 104 seated in the pulmonary arteries 12. See FIGS. 14 and 15. As best shown in FIG. 15, the entire anchoring section 109 assumes a ball-shape configuration when it is fully expanded, with the widest diameter portions (i.e., the vertex area 104) extending into the pulmonary arteries 12 to secure the anchoring section 109 in the region where the pulmonary trunk 10 branches into the pulmonary arteries 12, FIG. 15 also shows the capsule 2010 being further withdrawn to release the leaflet support section 102 inside the pulmonary trunk 10 at the location of the pulmonary valves 13. When the frame 101 is expanded, it becomes separated from the inner core 2025. FIG. 16 shows the assembly 100 being fully deployed in the pulmonary trunk 10, and with the distal tip 2015 and capsule 2010 being withdrawn with the rest of the delivery system.

Thus, when the assembly 100 is deployed, the ball-shaped configuration of the anchoring section 109 allows the leaflet support section 102 (and the leaflet assembly carried thereon) to be retained inside the pulmonary trunk 10 without the use of any hooks or barbs or other similar securing mechanisms. The tubular skirt 122, top skirt 120, and bottom skirt 121 together function to create a "seal" to prevent leakage (blood flow back from the pulmonary artery to the right ventricle from the area surrounding the assembly 100. In addition, the leaflet support section 102 pushes aside the native pulmonary valve leaflets 13 against the wall of the pulmonary trunk 10.

The assembly 100 of the present invention provides a number of benefits. First, the manner in which the leaflet support section 102 is anchored or retained in the pulmonary trunk 10 provides effective securement without the use of barbs or hooks or other invasive securement mechanisms. The securement is effective because it minimizes up and down migration of the assembly 100. This is important because this prevents portions of the leaflet support section 102 from extending into the right ventricle. Since the ventricle experiences a lot of motion during the operation of the heart, having a portion of the leaflet support section 102 extending into the ventricle may cause damage to the ventricle. Second, there is a wide variation in RVOT morphologies, so that the sizes of different patients' pulmonary trunks will vary widely. The configuration of the assembly 100 allows the assembly 100 to cover a greater range of diameters and lengths of the pulmonary trunk, thereby reducing sizing problems by allowing each model or size of the assembly 100 to be used with a greater range of patients.

Figure 17:
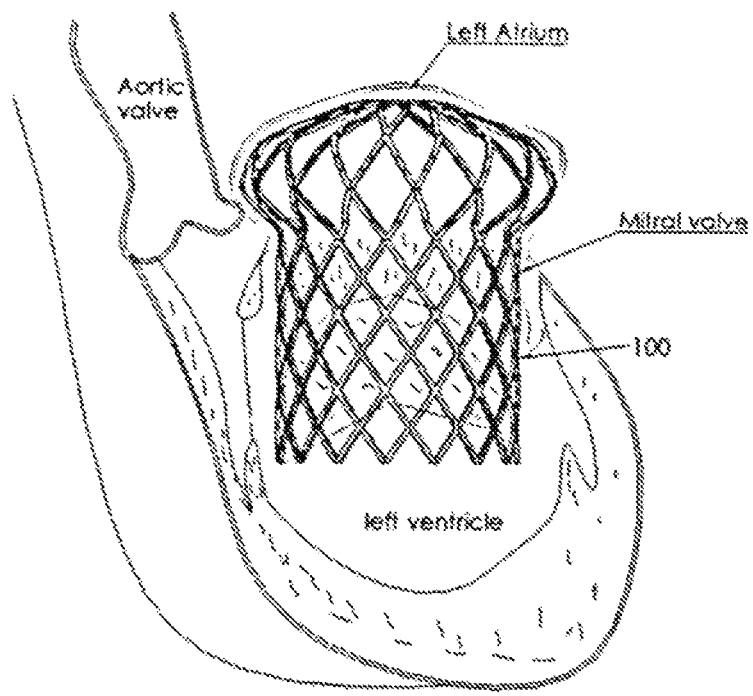
FIG. 17 illustrates the assembly of FIG. 1 deployed in the mitral position of a human heart.

Even though the present invention has been described in connection with use as a pulmonary replacement valve, the assembly 100 can also be used as a mitral valve, as shown in FIG. 17.

Figure 18:
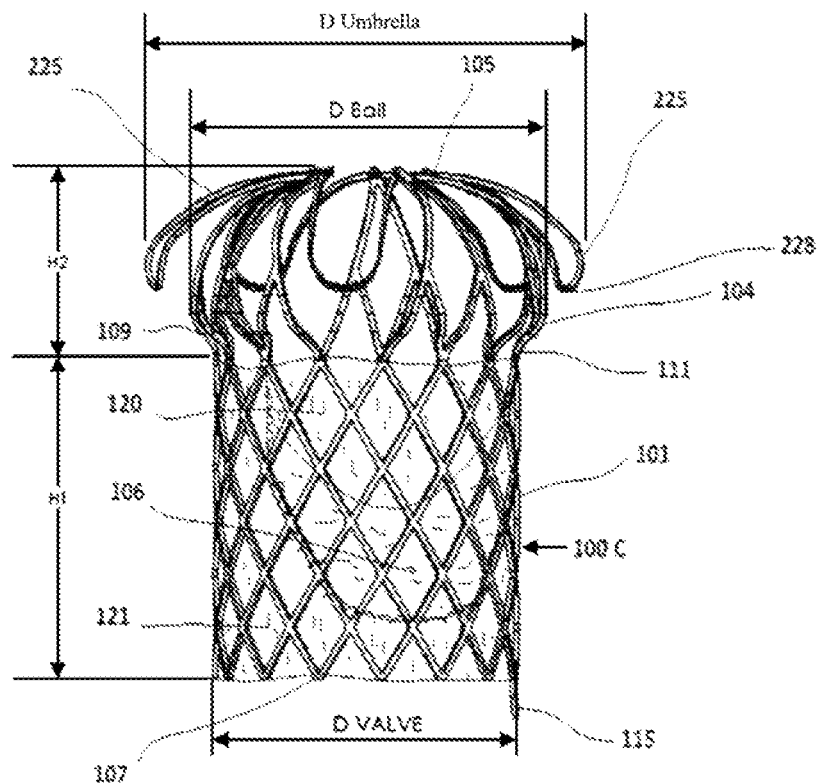
FIG. 18 is a side view of a pulmonary valve assembly according to another embodiment of the present invention shown in an expanded configuration.
Figure 19:
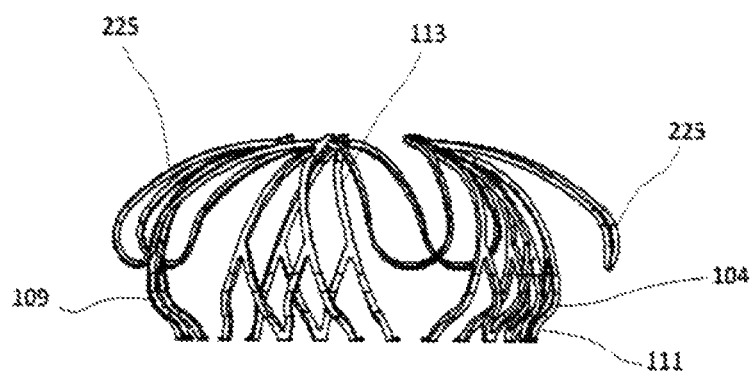
FIG. 19 is a side view of a portion of the assembly of FIG. 18.
Figure 20:
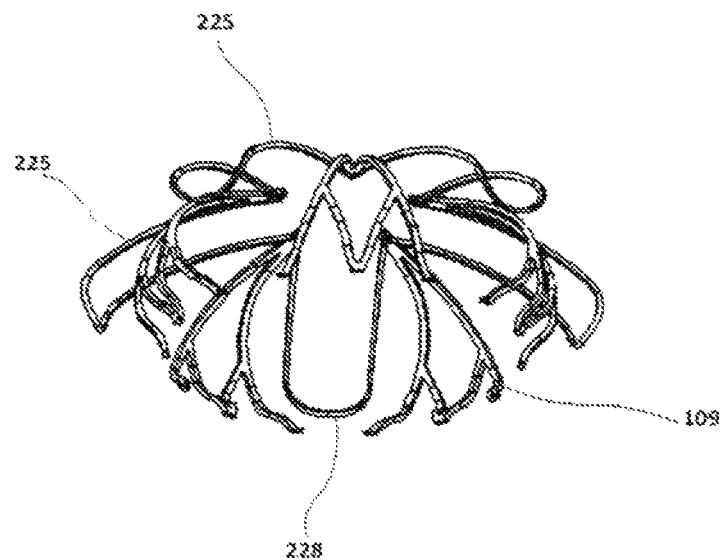
FIG. 20 is a perspective view of a portion of the assembly of FIG. 18.
Figure 21:
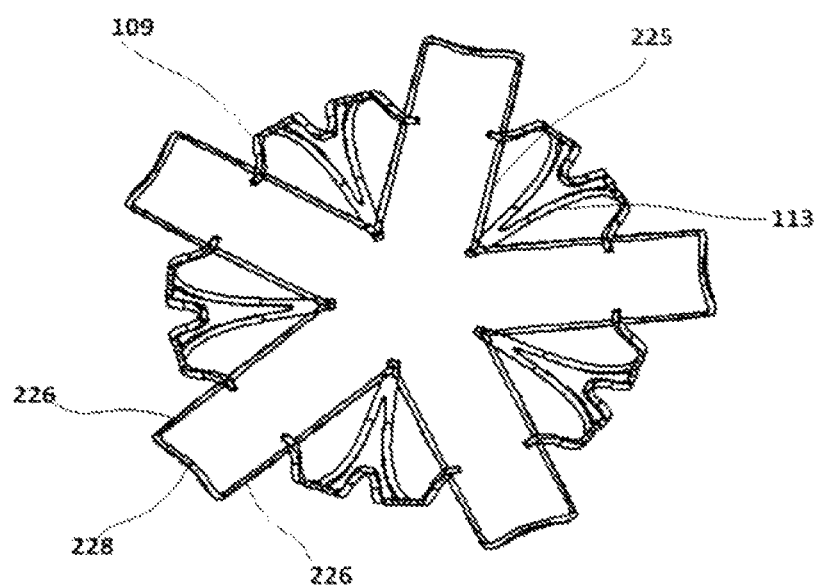
FIG. 21 is a side view of a portion of the assembly of FIG. 18.

FIGS. 18-22 illustrate a second embodiment according to the present invention. The assembly 100c shown in FIGS. 18-22 is the same as the assembly 100 shown in FIGS. 1-17 except that a plurality of umbrella segments 225 are added to the anchoring section 109. Each umbrella segment 225 is generally U-shaped in configuration (see FIG. 21) and has opposite side bars 226 extending from the hub 105. The opposing side bars 226 of each umbrella segment 225 are connected by an end bar 228. The umbrella segments 225 can be made from a single piece of wire or material, or each umbrella segment 225 can be made from its own separate wire or material. As best shown in FIGS. 18 and 19, each umbrella segment 225 extends radially outwardly from the hub 105 in a manner such that each umbrella segment 225 provides a canopy effect to cover the vertex area 104 of the anchoring section 109. In this regard, the outer circumferential diameter of the combined umbrella segments 225 is greater than the outer diameter of the combined vertex area of the anchoring section 109. Even though FIGS. 18-21 show five umbrella segments 225, it is possible to provide another number of segments, such as three, four, six or more.

Figure 22:
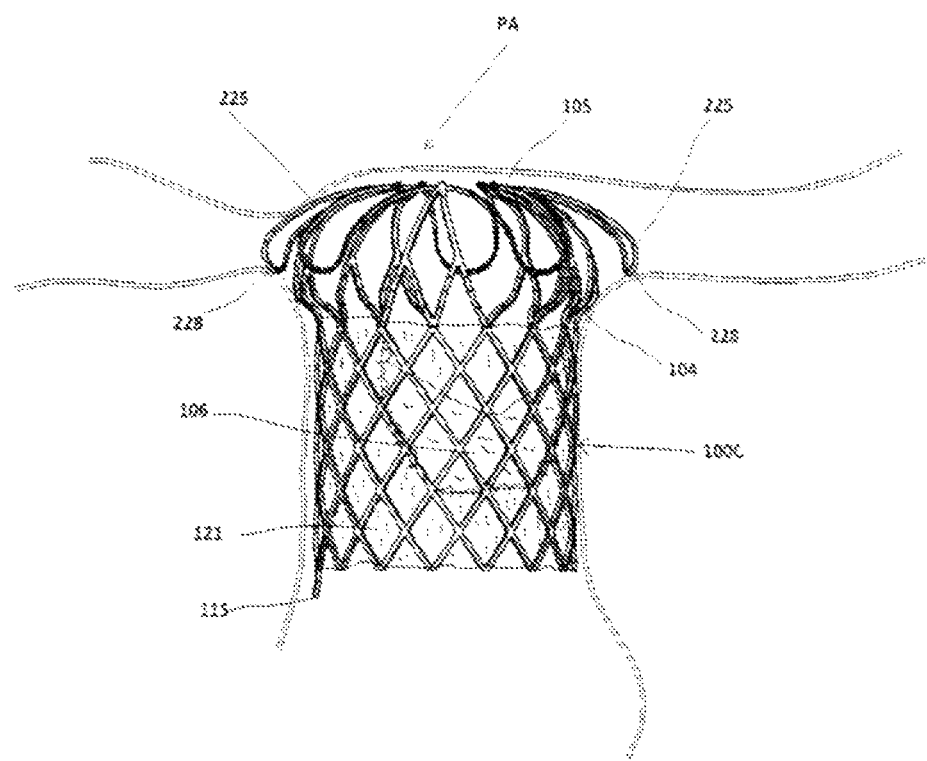
FIG. 22 illustrates the assembly of FIG. 18 deployed in the pulmonary trunk of a human heart.

As best shown in FIG. 22, the umbrella segments 225 function to provide more effective anchoring of the anchoring section 109 inside the wall of the pulmonary trunk 10. The end bars 228 of the umbrella segments 225 are adapted to seat or engage on the pulmonary artery (PA), thereby preventing the assembly 100 from slipping into the pulmonary trunk 10.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A pulmonary heart valve assembly, comprising:
   a frame comprising an anchoring section, a generally cylindrical leaflet support section, and a neck section that transitions between the anchoring section and the leaflet support section, the anchoring section having a circumferential vertex area defined by a plurality of wires that extend from the leaflet support section, with each wire extending radially outwardly to the vertex area, and then extending radially inwardly to a hub, the vertex area having a circumferential diameter, the anchoring section further including a plurality of umbrella segments that extend radially outwardly from the hub towards the leaflet support section and having a circumferential diameter that is greater than the circumferential diameter of the vertex area, and wherein each umbrella segment has two side bars that extend from the hub, and an end bar that connects the two side bars; and
   a leaflet assembly having a plurality of leaflets that are directly stitched to the leaflet support section.

2. The assembly of claim 1, wherein the leaflet support section has an inflow end that is configured with an annular zig-zag arrangement that defines peaks and valleys.

3. The assembly of claim 2, wherein the leaflet support section includes a plurality of ears that are provided at its inflow end.

4. The assembly of claim 1, wherein the anchoring section, the neck section and the leaflet support section are all provided in a single piece.

5. The assembly of claim 1, wherein the plurality of leaflets comprises three or four leaflets.

6. The assembly of claim 1, wherein the plurality of wires at the hub define an annular arrangement having a plurality of spaced-apart connection points, wherein each side bar extends radially outwardly from a connection point.

7. The assembly of claim 6, wherein the annular arrangement has a circumferential diameter that is smaller than a circumferential diameter of the leaflet support section.

8. The assembly of claim 6, wherein the annular arrangement has a circumferential diameter that is smaller than the circumferential diameter of the umbrella segments.

9. The assembly of claim 6, wherein the two side bars of each umbrella segment are connected with two respective adjacent connection points.

10. The assembly of claim 6, wherein adjacent pairs of wires converge towards the connection point at their upper ends before the connection point merges into the hub.

11. The assembly of claim 6, wherein the anchoring section has alternating large cells and smaller cells in a circumferential direction.

12. The assembly of claim 11, wherein each of the umbrella segments is radially aligned with one of the large cells.

13. The assembly of claim 1, wherein the umbrella segments cover at least a part of the anchoring section in an axial direction.

14. The assembly of claim 1, wherein the umbrella segments cover the vertex area of the anchoring section.

15. The assembly of claim 1, wherein each umbrella segment is generally U-shaped in configuration.

16. The assembly of claim 1, wherein the anchoring section has a ball-shaped configuration defined by the plurality of wires.

17. The assembly of claim 1, wherein an axial height of the leaflet support section is higher than an axial height of the anchoring section.

18. The assembly of claim 1, wherein an axial height of the anchoring section is higher than an axial height of the umbrella segments.

19. The assembly of claim 1, wherein the umbrella segments are made from a single piece of wire or material, or each umbrella segment is made from its own separate wire or material.

20. The assembly of claim 1, wherein the plurality of umbrella segments comprise three, four, five, or six umbrella segments.

* * * * *